United States Patent
Peterson et al.

(10) Patent No.: US 10,472,032 B2
(45) Date of Patent: Nov. 12, 2019

(54) AUTONOMOUS WATER COLUMN PROFILER

(71) Applicant: CSA Ocean Sciences, Inc., Stuart, FL (US)

(72) Inventors: Kevin C. Peterson, Stuart, FL (US); Jodi N. Harney, Fort Pierce, FL (US)

(73) Assignee: CSA OCEAN SCIENCES, INC., Stuart, FL (US)

( * ) Notice: Subject to any disclaimer, the term of this patent is extended or adjusted under 35 U.S.C. 154(b) by 164 days.

(21) Appl. No.: 15/839,036

(22) Filed: Dec. 12, 2017

(65) Prior Publication Data
US 2018/0162501 A1    Jun. 14, 2018

Related U.S. Application Data

(60) Provisional application No. 62/433,317, filed on Dec. 13, 2016.

(51) Int. Cl.
| | |
|---|---|
| *B63C 11/52* | (2006.01) |
| *B63G 8/00* | (2006.01) |
| *G01N 33/18* | (2006.01) |
| *G01N 1/02* | (2006.01) |

(52) U.S. Cl.
CPC ............. *B63C 11/52* (2013.01); *B63G 8/001* (2013.01); *G01N 33/1886* (2013.01); *B63G 2008/004* (2013.01); *B63G 2008/005* (2013.01); *G01N 2001/021* (2013.01)

(58) Field of Classification Search
None
See application file for complete search history.

(56) References Cited

U.S. PATENT DOCUMENTS

| | | | |
|---|---|---|---|
| 4,157,657 A | 6/1979 | Hinchman | |
| 5,816,874 A | 10/1998 | Juran et al. | |
| 7,690,247 B1 | 4/2010 | Lapota et al. | |
| 8,875,645 B1 | 11/2014 | Webb et al. | |
| 9,404,906 B2 | 8/2016 | Thomas et al. | |
| 10,322,783 B2 * | 6/2019 | Valsvik | B63G 8/001 |
| 2003/0092393 A1 | 5/2003 | Tokhtuev et al. | |
| 2010/0302901 A1 * | 12/2010 | Welker | G01V 1/3843 367/21 |

(Continued)

FOREIGN PATENT DOCUMENTS

WO     03/012434 A2    2/2003

*Primary Examiner* — Natalie Huls
*Assistant Examiner* — Jermaine L Jenkins
(74) *Attorney, Agent, or Firm* — Duane Morris LLP (57) ABSTRACT

Autonomous water column profilers are deployed over an area and each independently samples attributes in its water column to provide a three dimensional array of data points. The profilers are negatively buoyant and autonomously assume positive buoyancy; for example, by jettisoning a ballast weight, preferably collecting and storing measurements at programmed times or depths when descending and again when ascending. The devices can be recovered for accessing onboard memories or a wireless communications system can be employed for uploading data to a transponder. The profilers can be deployed from marine vessels, aircraft, or remotely operated vehicles and are advantageous for monitoring oil well leaks or spills, assessing dispersant programs when ameliorating released oil, for sensing natural seeps, and similar applications.

20 Claims, 7 Drawing Sheets

(56) References Cited

U.S. PATENT DOCUMENTS

2014/0053768 A1* 2/2014 Brizard ................ B63G 8/001
    114/321
2014/0290554 A1* 10/2014 Brizard ................ B63G 8/001
    114/331
2014/0301161 A1* 10/2014 Brizard ................ B63G 8/001
    367/15
2015/0336645 A1* 11/2015 Brizard .................. B63G 8/22
    701/21
2017/0240257 A1* 8/2017 Brandt ................. B63G 8/001

* cited by examiner

AUTONOMOUS WATER COLUMN PROFILER

CROSS REFERENCE TO RELATED APPLICATION

This application claims the priority of U.S. Provisional Application Ser. No. 62/433,317, filed Dec. 13, 2016, the contents of which are hereby incorporated by reference.

FIELD OF THE INVENTION

This disclosure concerns marine sensing apparatus and methods, in particular a readily handled small, lightweight but functionally autonomous data collection device that can be deployed by hand from a small vessel, fixed platform or aircraft. The autonomous device is configured to travel through a preset depth of a water column by controllably varying its own buoyancy, and to measure the values of various parameters at predetermined times or locations. As non-limiting examples, values for depth or pressure, GPS coordinates, temperature, salinity, pH, fluorescence (concentration of hydrocarbons and other organic matter), dissolved oxygen concentration, or concentration of other chemical compounds are collected in situ and stored in memory on-board the autonomous device. Upon reaching a programmed depth (or the seafloor or a predetermined elapsed time), the apparatus autonomously adjusts its buoyancy (for example, by jettisoning ballast) so as to autonomously return to the sea surface for recovery and/or for reporting collected data (in on embodiment by iridium satellite telemetry).

The apparatus and methods are particularly useful to the oil and gas industry in three primary ways: rapid response monitoring of the water column following accidental oil releases from offshore infrastructure in shallow to deep water; regular monitoring of water column conditions in the area of an offshore well, production platform, or other facility; and exploration of the water column for indicators of natural hydrocarbon seeps in the deep ocean. A number of autonomous data collection sensors can be deployed in a spatial array, each for profiling parameters at one or many depths in their respective water column (from the sea surface to near the seafloor) that may be affected by petroleum drilling activity or by natural phenomena. The ability to deploy and retrieve the apparatus from a small vessel, fixed platform, or aircraft without requiring deck equipment such as lifting apparatus, enables the collection of data from remote areas, in a timely fashion, and without the need for a large or complex vessel or deployment system. With minimal instruction or training, offshore personnel can deploy the device, or an array of the devices spaced in a line or grid, without extensive training, complex programming duties or operational requirements.

PERTINENT ART

Offshore oil and gas exploration and production activities can benefit from having rapidly deployable oil spill response tools available. It is conventional to have various sensors and instrumentation associated with exploration and production apparatus itself, for example fixed sensors. The present disclosure provides techniques for in situ monitoring of the water column from the sea surface to the seafloor in deep water environments, using relatively inexpensive and efficient autonomous devices that can be deployed, for example, in a pattern surrounding a location of interest or along a known water current pathway relative to a well or other location of interest, and for sampling conditions at programmed depths and/or times. The collected data allow oil spill responders to identify and track subsurface oil plumes over space and time, to test model predictions, and to understand the efficacy of subsea dispersant injection (SSDI) when used as a response tactic, among other examples.

Both natural and human activities can cause subsea emissions that are advantageously monitored for various reasons. Certain effects that are likely to arise in the area of an uncontrolled subsea well or leak and subsequent effects of using SSDI as a response tactic are discussed herein as examples. Dispersant advantageously reduces the size of oil droplets and inhibits their rise to the sea surface. This reduces threats to workers at the surface and also vital resources at the shoreline, by keeping more released oil in the subsurface environment. It is both advantageous and reasonably required to monitor and control such injections and their effects in order to optimize results. The invention is likewise applicable to other monitoring scenarios, such as natural seeps, natural biological events such as algae blooms, and the effects of nutrient loading on dissolved oxygen levels in the marine environment.

Subsurface hydrocarbons in the marine environment are conventionally detected using fluorometers and dissolved oxygen sensors that are deployed from a ship using a custom electromechanical cable and real-time communication of sensed parameter data. Other devices, such as Gliders, Autonomous Underwater Vehicles (AUVs), and Remotely Operated Vehicles (ROVs) are also used to deploy sensors for data collection, but are larger, more complicated machines which require deck equipment and lifting devices for deployment and retrieval. These advanced vehicles are also expensive, difficult to obtain on short notice, require advanced training to program and deploy, and require multiple operators for deployment. Deployments are typically slow and are limited by the number of vessels that need to be equipped and deployed for the project (typically only one or two vessels based on equipment availability and cost). The spatial positioning and resolution of the information is thus typically limited to the route of the equipped vessels and to conditions that may impede the work of the vessel and on-board personnel, not the least of which is the travel time that a suitably equipped large vessel may need to reach the site of interest. However, the time window over which these monitoring data are required is crucial and brief, owing to the ephemeral nature of the hydrocarbons in the marine environment. Delays in monitoring the event are experienced owing to the time needed to equip, deploy, and mobilize the vessel to the area of interest.

It would be advantageous to enable monitoring to occur rapidly after an event and in a widespread area so as to produce a more useful understanding of the extent and limits of oil in the water column. It would also be advantageous if such monitoring could be accomplished with apparatus that operates autonomously when deployed quickly and simply at the sea surface, for example merely by dropping autonomous units into the water from an aircraft or small (fast) vessel at spaced locations along a line or grid.

SUMMARY OF THE INVENTION

It is an object of the present invention to improve arrangements that are available for sampling conditions to characterize a potentially substantial volume of water, in particular by enabling possibly numerous autonomous measurement devices to be deployed over a broad area and arranged by autonomous operations to drop through their local water column and collect in situ data along the way, then returning to the surface to transmit or otherwise report the results. In one scenario, a population of autonomous sensors can be dropped into the sea at a pattern of points around the location of a spill (before and after the injection of dispersants).

In addition to spill response, the rapid collection of in situ water column data over space and time is valuable in other exploration and scientific expeditions, such as those focused on locating and modeling hydrocarbon seeps on the sea floor.

For these applications, there is a need for a device that is capable of collecting data at multiple points through the three-dimensional space of entire water column from the sea surface to the sea floor, as well as over time. The collected data must then be accessible in near-real time to facilitate decision-making and planning of response, mitigation, monitoring and analysis of the site.

The locations of ocean operations or expeditions tend to be remote, and can be in thousands of feet of water. In the case of an oil spill, time is of the essence. The time to identify, contract, mobilize, and transit an appropriate vessel to the incident site can be measured in days or weeks. The challenge is to have the ability to begin the collection of data within hours of an event, providing decision makers with vital information long before the first vessels arrive on location with more traditional sampling equipment. There is a need for a relatively low-cost preferably hand-deployed device that can be launched and retrieved from aircraft, small vessels, fixed platforms, and other marine assets, without specialized lifting equipment or deck equipment, and that can be on site long before other traditional cabled and autonomous systems can be deployed. The cost factor and the small form of the apparatus allows multiple units to be deployed simultaneously from various platforms and locations by personnel that do not require substantial advanced training.

There is also a need to produce three-dimensional models of the incident area and surroundings to guide response and mitigation procedures. Traditional data collection methods utilizing the deployment of sampling devices and sensors with oceanographic winches and cables, Remotely Operated Vehicles (ROVs), Autonomous Underwater Vehicles (AUVs), Autonomous Surface Vessels (ASVs), and various types of wave and buoyancy gliders can produce valuable data but require more time to plan, mobilize, and implement deployment, require a far larger and more expensive operational footprint, and demand more time to retrieve and process data. In some cases, traditional equipment may not be available in the area and could be extremely expensive to mobilize. It would be advantageous to enable rapid and versatile data collection so as to be capable of producing an appropriate "3D Snapshot" of a site of interest, preferably in a convenient and inexpensive manner whereby it is readily possible to repeat and/or adjust the measurement protocol for determining change in the site over time.

BRIEF DESCRIPTION OF THE DRAWINGS

There are shown in the drawings certain embodiments and arrangements as discussed herein, which are non-limiting examples of the invention and its applications. It should be understood that the invention is not limited to these examples and is capable of variation within the scope of the appended claims. In the drawings:

FIG. 6 is a deployment and decision flow chart to describe the deployment, operation, and retrieval of the device and data according to an exemplary embodiment. FIG. 6 is divided for clarity into sequentially connected sections 6A and 6B.

DETAILED DESCRIPTION

It is an aspect of the invention to specify and provide a readily deployable marine sensing apparatus that is practical to deploy, for example by hand, at a site of interest preferably as one of an array of plural units, each capable of sampling and sensing conditions at desired locations in a study area, and at predetermined multiple depths. In exemplary deployments, the device can be deployed from an oil and gas rig, helicopter, or vessel. Advantageously, plural devices are deployed, each spaced from the next along a line and/or laterally. When dropped to the water surface, the device preferably collects location data by satellite communication. The autonomous device sinks through the water column repetitively collecting in and storing situ data at depth until it reaches a specified depth (or the bottom), at which point it autonomously adjusts its buoyance, e.g., by releasing ballast weight, and returns to the surface. At the surface, the device collects its position and reports its stored data, for example transmitting identity, location and measurement data via satellite. Data transmissions are intercepted by web-based spatial mapping software (known as an Environmental Common Operating Picture). The information can be shared with a Command Center working to mitigate the spill by controlling spill amelioration techniques, in which case the information provides valuable feedback on needs for further mitigation and efficacy of mitigation steps taken.

Figure 1:
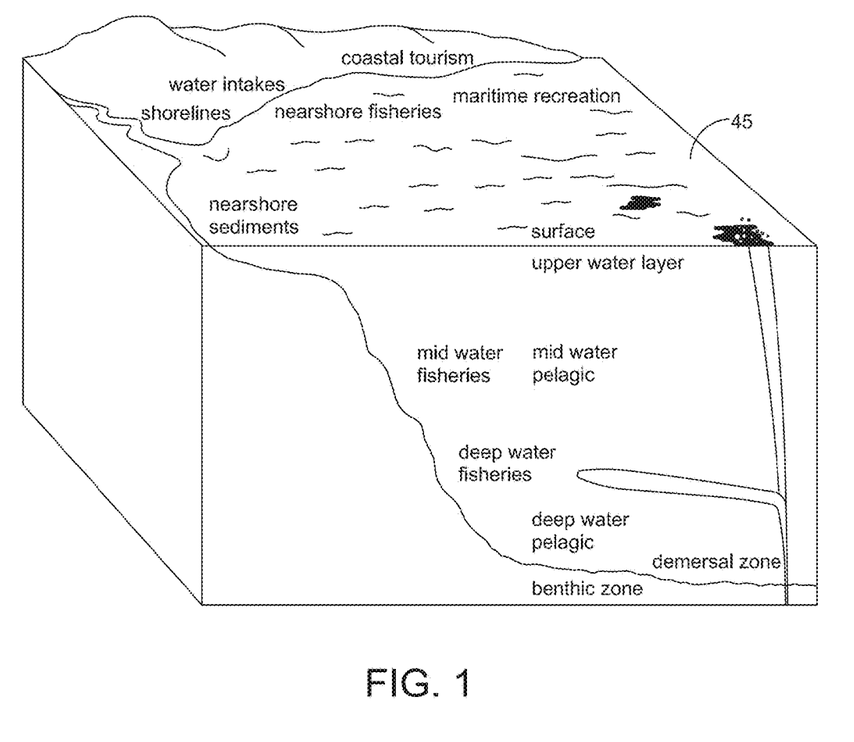
FIG. 1 is a schematic perspective view of a theoretical volume of ocean water in which the invention may be advantageously deployed. This drawing illustrates certain effects of subsea dispersant injection (SSDI) at a wellhead, effectively increasing the concentration of released oil in the subsea environment while decreasing the amount of oil on the sea surface and moving toward shore.
Figure 3:
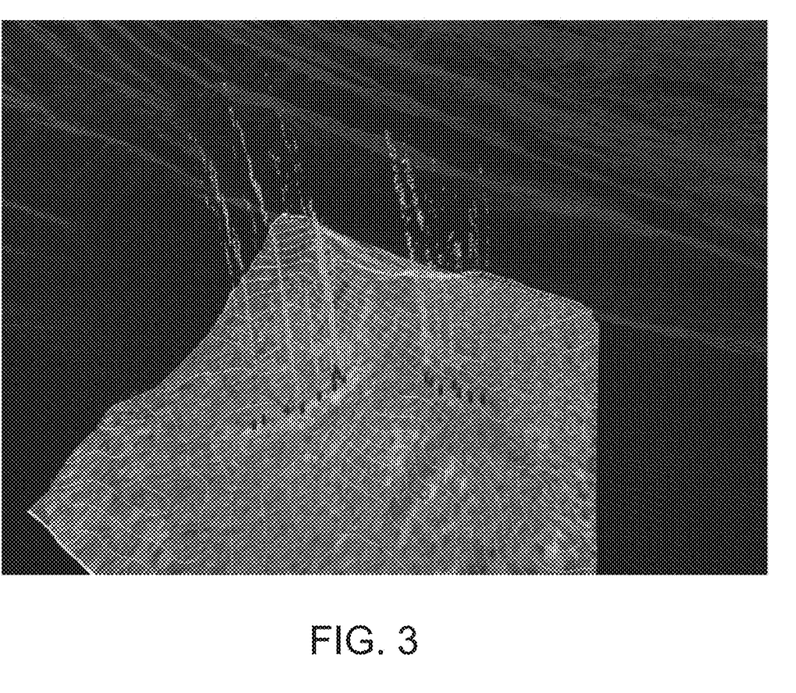
FIG. 3 is a graphic illustration of 17 gas seeps (plumes) that were identified east of Cape Henry, Va., using multi-beam sonar built into the hull of the government research ship Okeanos Explorer. (Image source: National Oceanic and Atmospheric Administration, 2012 (http://www.noaanews.noaa.gov/stories2012). This graphic shows exemplary natural conditions supplementing FIG. 1.
Figure 4:
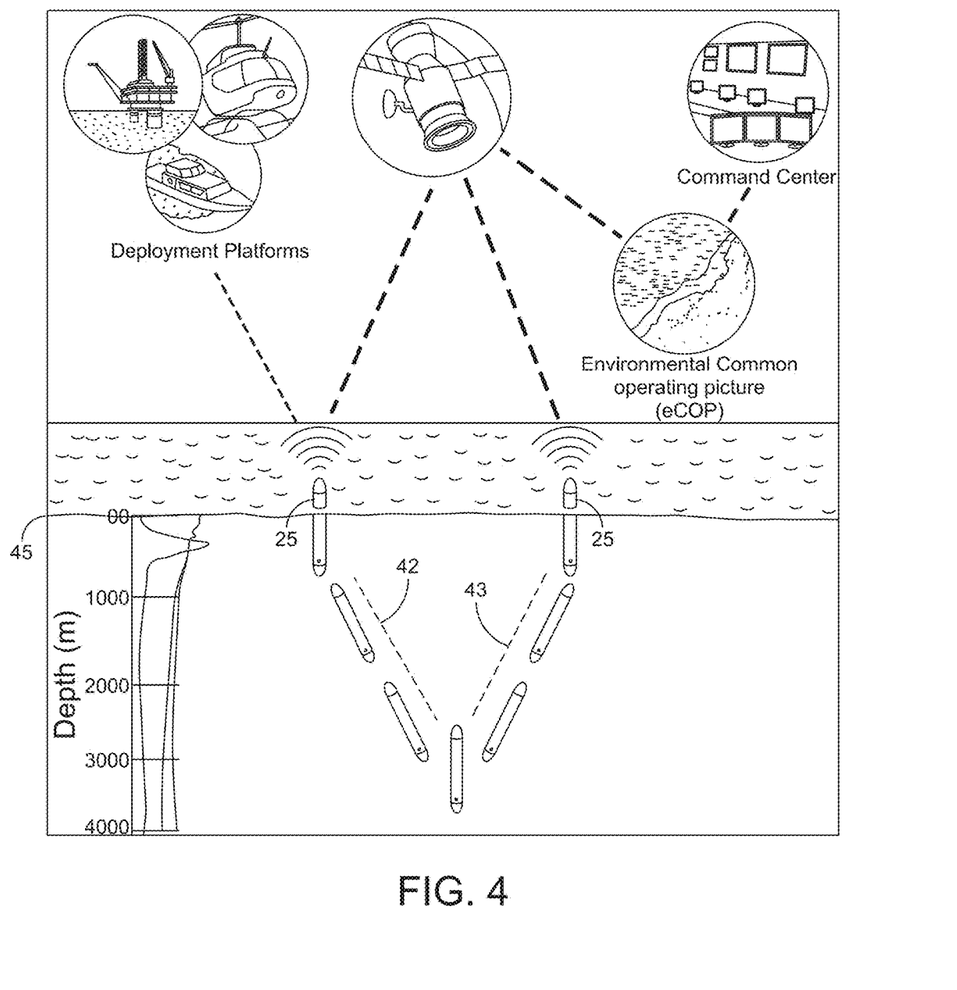
FIG. 4 is a schematic illustration demonstrating aspects of deployment and operation of one or more of the autonomous devices.
Figure 6A:
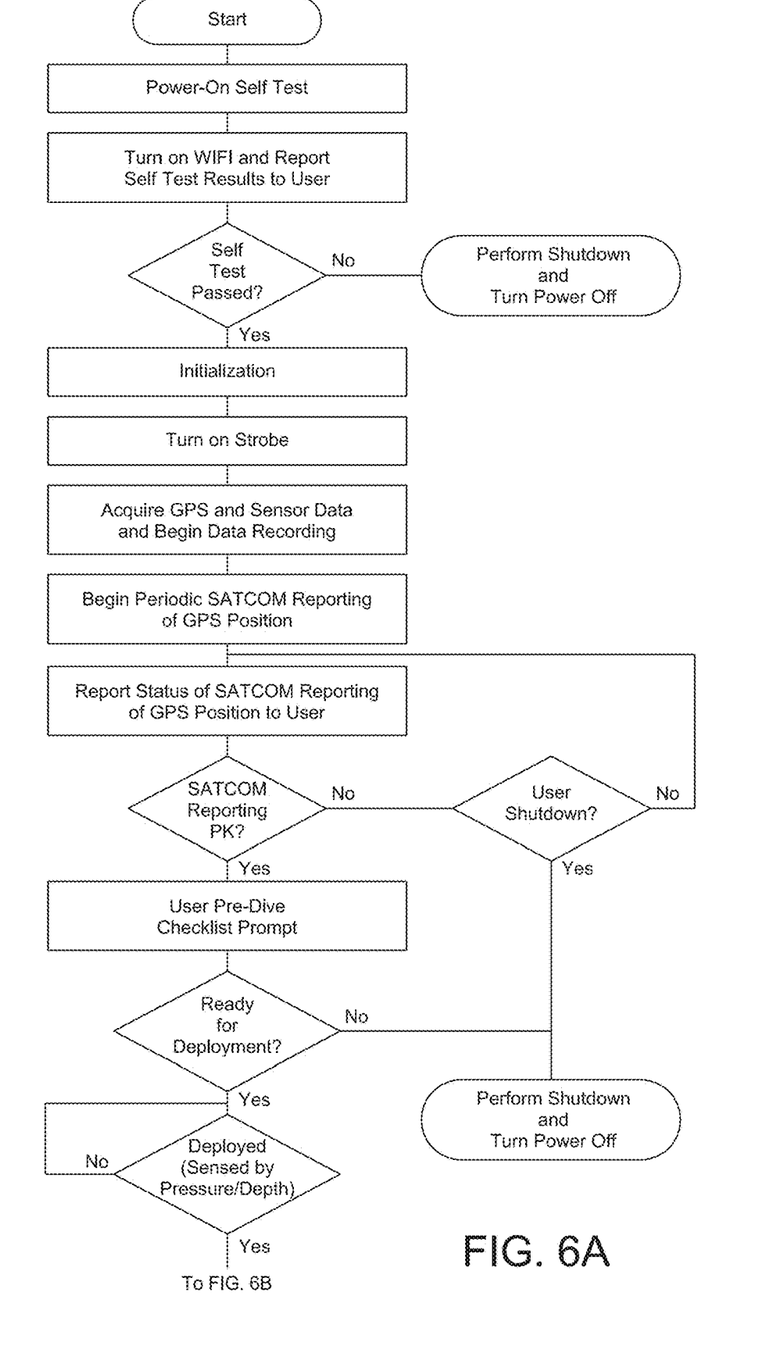

FIG. 1 shows conditions in an arbitrary marine site associated with petroleum drilling activity and a theoretical leak. FIG. 3 shows real life gas seepage conditions (detected using sonar). FIG. 4 shows a schematic of deployment and operation of the device in the ocean. FIG. 6 shows a conventional flow chart to describe the internal and external procedures and decisions involved in deployment, data gathering, and retrieval.

In one embodiment, the apparatus comprises an autonomous sensing and data collection apparatus with an onboard controller. One such apparatus, or preferably an array of apparatus distributed over an ocean surface area, is released at the surface and allowed to effect a predetermined sequence of activities including taking ambient parameter measurements while descending through a water column; for example, spaced according to incremental depths or at programmed time intervals or at predetermined target depths and/or times. Upon completion of the predetermined sequence, the apparatus autonomously adjusts its buoyancy by releasing ballast or displacing water in ballast tanks using pressurized gas, so as to return to the ocean surface. At the surface, the data is collected either by data communications between a central collection facility and the autonomous apparatus, or by physically recovering the autonomous apparatus and obtaining data from one or more data storage elements that are carried thereon.

The apparatus comprises an underwater pressure resistant housing, a suite of sensors, a battery pack, a wireless communications system, a buoyancy module, a ballast weight, and a mechanism configured to release the ballast weight at a predetermined depth and/or time, whereupon the device returns to the surface due to its onboard buoyancy.

Figure 6B:
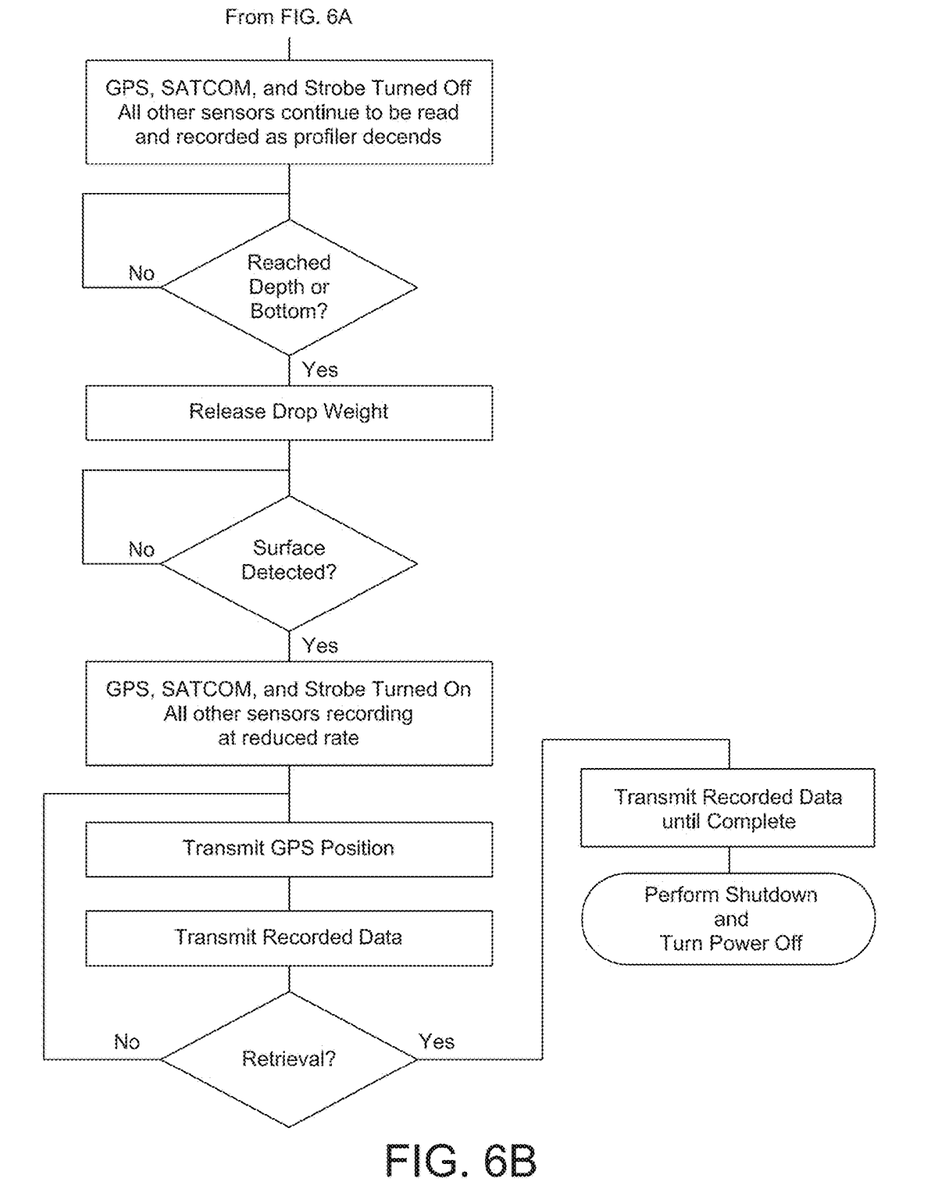

According to the examples discussed herein, deployable marine sensing devices as described are readily deployed in the ocean from a variety of platforms and can be optimized, for example, for deployment from marine vessels, aircraft, and/or remotely operated vehicles. In the exemplary embodiment detailed in FIG. 6A, the device is powered on, and a self-test is conducted. Wireless (WiFi) is powered, and a report of the self-test results is transmitted to the user. If the report is negative, the user will power off the device and attempt reprogramming. If the report confirms readiness, the user initializes the device, turns on the strobe, and allows the device to acquire GPS and sensor data, recording the information to the on-board MicroSD data storage 33. The device begins periodically reporting its GPS position using satellite communication, and will report this status to the user. Once satellite communications are confirmed, the user is prompted through a pre-dive checklist. The user commences deployment (manually dropping the device to the water surface from the deployment platform). When initially deployed, each device is negatively buoyant and sinks through the water column, collecting and recording data from the suite of onboard sensors. As shown in FIG. 6B, the device automatically ceases GPS data collection, satellite communications, and strobe function when deployed (sensed by reaching a predetermined pressure/depth). All other sensors continue to collect data at preset intervals during the descent through the water column as shown in FIG. 4. Once the device reaches the seafloor, or a predetermined depth selected as a programmed pressure criterion or point in time, the device jettisons a ballast weight (releases drop weight as shown in FIG. 6B), rendering the device positively buoyant. The device floats to the surface. The on-board pressure sensor detects the surface pressure, whereupon the device automatically restores power to GPS, satellite communications, and strobe sections. All other sensors continue to collect data but at a reduced predetermined rate. While drifting at the surface, the device transmits via satellite communications the on-board collected data and GPS position such that the device can be retrieved and reused. The device will continue to transmit data until complete. The device continues to transmit GPS position until it is retrieved and shut down by the user.

The autonomous water column profiler (AWCP) as detailed herein is portable, easily deployable, and autonomous according to programming of movement and activities including movement, sensing, and data reporting. No conductive, electromagnetic, sonar based or other signal paths are required during the subsurface phase of the deployment because the device is programmed to proceed autonomously through its traversal of the water column and data collection process. The device is equipped with sensors to collect data on the in situ physical and chemical characteristics of the water column from the sea surface to the sea floor. The sensors can be modular and selectively employed as needed for particular projects. On board data storage illustrated in FIG. 5, along with signaling and data transmission capabilities, enable the device to achieve several key goals and to meet the requirements and challenges of efficiently sampling conditions in a volume of water in a marine environment.

According to exemplary embodiments, the AWCP has operational characteristics and capabilities including:

Rapid mobilization to a remote site

Deployment from aircraft, marine vessels, and remote vehicles

Collects in situ data from the sea surface to the sea floor

On-board power to support autonomous data collection and transmission

No need for the deployment craft to remain on site after system deployment

Tracking and/or location sensing capability to facilitate ongoing modelling and unit retrieval Transmits data through wireless communications to remote locations Easy replacement of power module and reconditioning of ballast unit for quick redeployment Versatile suite of sensors that can be interfaced to the system Among other technical aspects, the AWCP unit is characterized by:

Size and weight allowing manual or automatic handling and deployment from a variety of platforms. In an exemplary embodiment, the external dimensions are approximately 34.5 inches in length by 4.5 inches in diameter. The approximate weight of each device including the drop weight is 17 pounds. Dimensions and weights will differ slightly depending on specific configuration.

A basic unit rated to traverse 4000 meters depth of seawater, with customized units enabling the depth range to be expanded to maximum encountered depths A programmed controller coupled to sensory and mobility facilities, with a capability to proceed through at least one sampling passage from surface deployment to a maximum depth and return to the surface, optionally programmable to effect multiple such passages.

Resetting for deployment is possible with or without physical connection to programming interface. That is, if data are offloaded wirelessly, the device can be reset with a simple switch and physical replacement of ballast weight.

Additional programmable settings are available such as sensor data collection rates (up to 4 Hz for some sensors) and/or depth-dependent sensor operation.

Additional data on ambient subsea, deepwater currents will be calculable from time, depth, acceleration, and location data processed through a custom algorithm following device retrieval.

The AWCP unit carries both ballast weight and buoyancy modules, at least one of which is responsive to programmed controls to enable deployment, traversal of the water column in down and up directions, and dwell at the surface for retrieval. In a one-passage embodiment, the ballast is coupled by a connection that enables the ballast to be released and jettisoned upon signalling from the controller.

Advantageously, the device is capable of data transmission and position reporting while on the surface via a satellite and/or radio frequency link. Alternatively, a signalling system can produce a ping or beacon permitting a surface vessel to readily track and recover the unit.

Sensor suite preferably is modularly configured or similarly configured to be modified depending on specific applications. In one embodiment adapted for oil/gas testing or production applications, the AWCP includes:

Geographic positioning system (GPS) for surface positioning

Fluorometer for detection of organic material (namely hydrocarbons) in water

Pressure sensor

Temperature sensor

Optical dissolved oxygen sensor

Accelerometer for tracking of position and movement

Data logger to store data from on-board sensors

The AWCP device is configured for airfreight and deployment into the ocean from small, medium, and large marine vessels, helicopters, and specially outfitted airplanes as well as a variety of remote controlled marine and remote controlled aircraft. Two operational examples (use cases) are described below.

In a first example, the AWCP is configured and deployed in connection with an actual or suspected oil spill from a subsea well. Assuming that a plume of oil is leaking from the well into the water column, the AWCP is used in conjunction with and for planning and monitoring the progress of a subsea dispersant injection (SSDI) operation to ameliorate effects of the spill as shown in FIG. 1. Responsible parties, responders, and other stakeholders deploy several AWCP devices in a spatial pattern to begin to identify the subsea plume of oil, to track its trajectory, to test model predictions of plume movement, and to monitor the effects of the dispersant injection operation, as quickly and effectively as possible.

A sampling plan and design are defined, including a predetermined number of devices and locations/spacing of device deployments. The sampling plan can be selected from a set of previously specified plans, and is carried out with the approval and cooperation of simultaneous operations (SIMOPS); for example, to coordinate the emission of dispersant at the wellhead and in its vicinity, and for other activities such as efforts to block and repair the source of the leak.

Depending on the location of the well site, its distance from shore, and availability of marine or aviation platforms, one or multiple deployment-ready AWCP devices are expeditiously transported to incident location. As shown in FIG. 4, the AWCP is launched from an available deployment platform to the ocean's surface. The ability to launch this device from small, readily available deployment platforms such as fast vessels, fixed installations such as drilling rigs, and aircraft is an advantageous feature of the device.

Each AWCP is deployed into the ocean and released for autonomous operation. The AWCPs each sink due to negative buoyancy, especially due to a ballast weight attached to the package. Once each device approaches or contacts the sea floor, or at a pre-programmed depth or time of deployment, the ballast weight is automatically released by the on-board control circuits. The device drifts back to the surface under positive buoyancy.

As described above and illustrated in FIG. 6, in a preferred arrangement, each AWCP is programmed to collect in situ data as a function of depth, during both the descent to the seafloor and the return ascent to the sea surface. On the surface (commencing upon detection of reaching the surface or at a programmed time, each device begins transmitting its GPS location via a satellite link to a central monitoring location, along with packets of the water column data collected during the descent and subsequent ascent.

Figure 5:
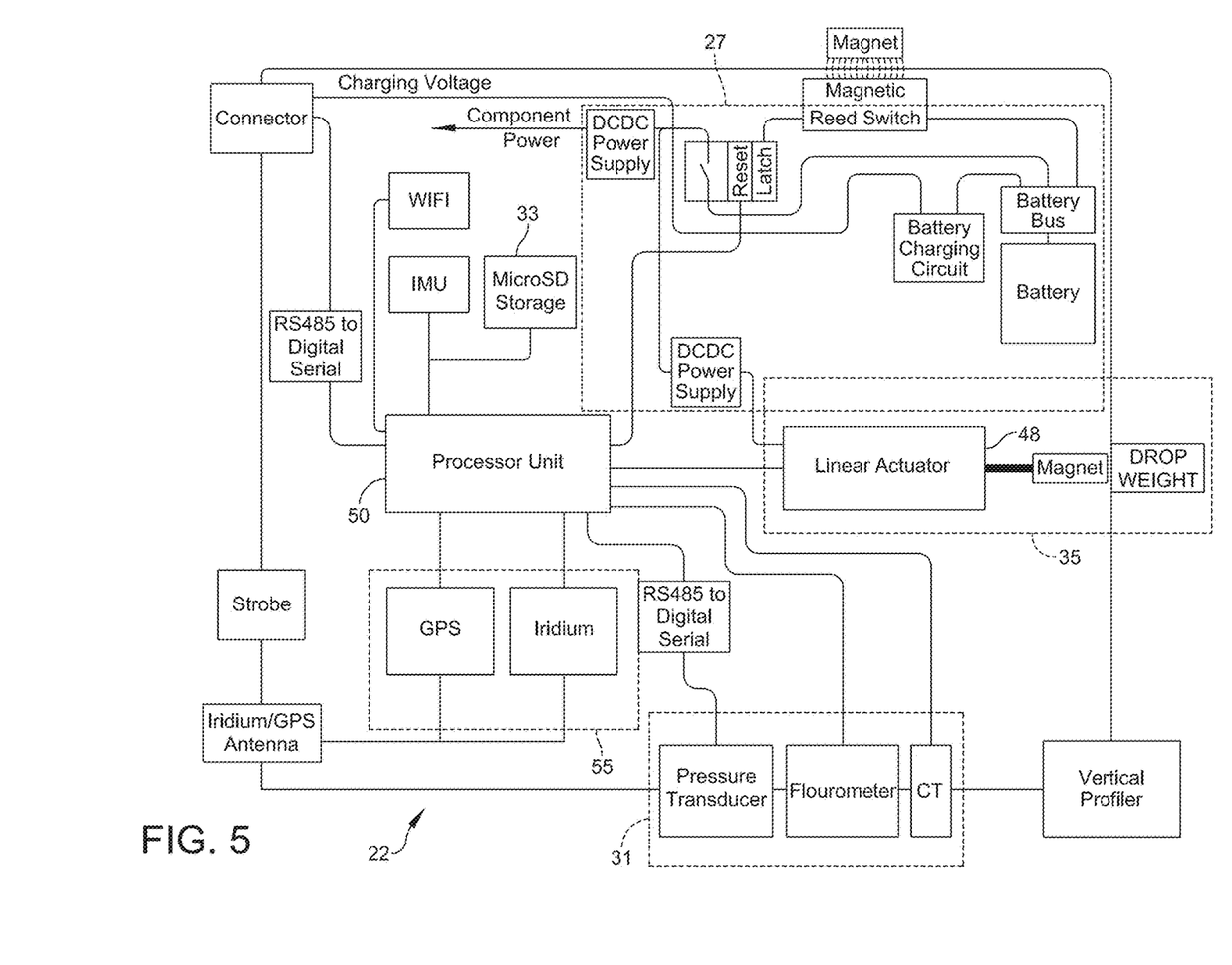
FIG. 5 is a block diagram of the apparatus in an exemplary autonomous device.

Once the device has returned to the surface, the pressure transducer reading (detecting surface pressure) alerts the processor unit to switch on the GPS and the iridium modules shown in FIG. 5, which begin to transmit identification data and location, and data that was stored during deployment from the MicroSD storage module, through the satellite link as illustrated in FIG. 4 to update the environmental common operating picture and the command center. As data are received at the command center or similar monitoring site for the incident or deployment, they will be processed to provide deployment location, real time location, data readings through the water column, a profile of the current in the area, and other physical and chemical readings throughout the water column. The sampling points and data readings from the AWCPs at an array of locations and depths enable a volume of water around a point of interest to be characterized, including changes over at least the time of descent and ascent. In the illustrated configuration, additional WiFi communications are supported, shown in FIG. 5, which can be used as an alternative short range communication path, for example for programming operational parameters to the device when on board or for short range data uploading during retrieval.

Deploying plural devices in a grid-like sampling design, either in one deployment or repeated deployments, enables construction of a three-dimensional model of the incident area, including over a window of time, the modelling and data being crucial to decision-makers and response planners.

One or more or all of the deployed AWCPs can be immediately retrieved, refurbished with a new ballast element and optionally a charged battery, and redeployed. Alternatively or in addition, one or more or all of the AWCPS can be left to drift with a surface oil slick, providing additional tracking data.

If the well continues to leak and dispersants are utilized, data collected from the AWCP devices enabled further planning, approval and monitoring of the use of SSDI as a response tactic.

In a second operational scenario, the AWCPs as disclosed are useful for monitoring oil and gas that may be released into the marine environment from natural seeps on the seafloor. Identifying seeps in the subsea environment may begin by collecting observations of oil slicks at the sea surface, measuring the variations in hydrocarbon concentrations in the water column, and acoustic detection of gas releases from the seafloor (as shown in FIG. 3).

Ship-mounted echo sounders have proven to be effective in the detection and mapping of bubble plumes in the water column. Acoustic surveys are designed to map the likely seabed origin and water column presence of gas plumes. These data provide seafloor target locations for inspection, sampling, and monitoring with additional in situ tools and sensors. Because seeps are typically intermittent and unpredictable, their characteristics and relative effects on the water column are of particular interest to the oil and gas industry, federal and state government agencies, and academic researchers.

Detection and characterization of seafloor seeps and the surrounding water column is limited by reliance on relatively slow, expensive, and spatially limited offshore operations. However, one or preferably and array of multiple AWCPs deployed in the vicinity of seeps, as described herein, rapidly supplies data to produce a three-dimensional characterizations of water column properties, similar to the application for oil spill response described above. A sampling design with a temporal component that allows for multiple redeployments in the area over time further improves the understanding of the effects of seeps on the water column, potentially leading to improvements in seep detection and characterization.

Accordingly, and with reference to the appended claims, the subject invention provides an autonomous marine data collection apparatus 22 having a data collection unit 25 configured for subsurface deployment, with an on-board power supply 27, a marine parameter value sensor 31, a data memory 33 and a variable buoyancy device 35. The variable buoyancy device 35 is configured to maintain a negative buoyancy condition for the data collection apparatus during at least one descending phase 42 of the subsurface deployment of the data collection apparatus, in which the data collection apparatus descends autonomously through a marine water column (FIG. 4), and to switch into a positive buoyancy condition during at least one ascending phase 43 of the subsurface deployment, in which the data collection apparatus 25 ascends autonomously to a marine surface. The parameter value sensor 31 is configured to measure at least one marine parameter value (e.g., pressure, fluorescence, etc.) encountered during at least one of the descending and ascending phases 42, 43 and to record said marine parameter value in the data memory 33. The data memory is configured for extraction of data in the data memory 33 following the subsurface deployment (FIG. 4 showing the example of satellite reporting).

Figure 2:
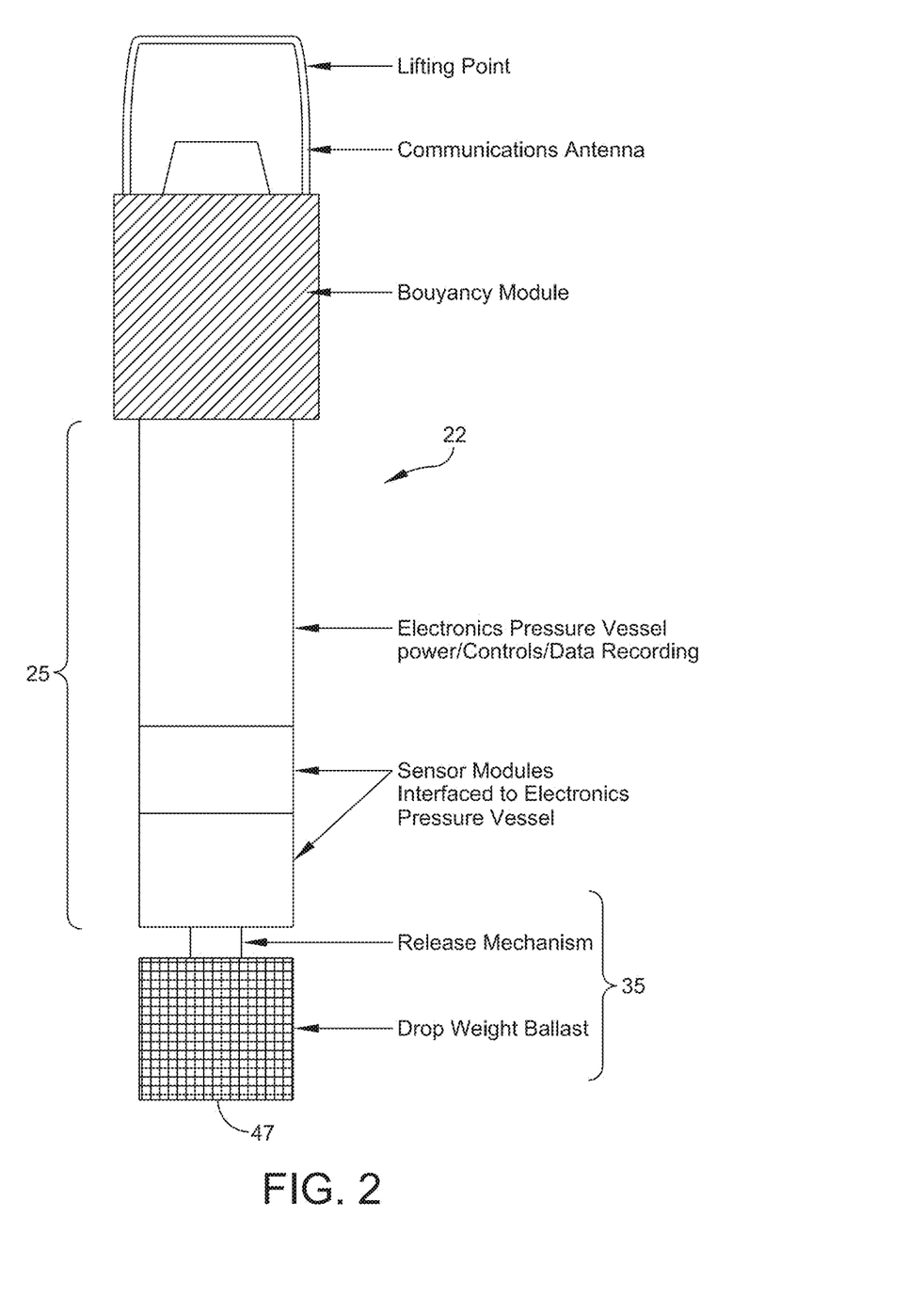
FIG. 2 is an elevation view showing the respective operational parts of an autonomous water column monitoring device according to the invention.

The data collection apparatus 25 is contained in a housing (FIG. 2) that contains or is affixed to the variable buoyancy device 35. The variable buoyancy device 35 is configured for one of releasing a ballast weight 47 and inflating a ballast plenum, when switching into the positive buoyancy condition for the ascending phase 43. In the embodiment shown in FIG. 5, a linear actuator is used to physically move a magnet for detaching engagement of the drop weight. Once the drop weight is detached, the unit is positively buoyant and begins its ascent to the surface.

In disclosed examples, the variable buoyancy device 35 is triggered by at least one mechanism: reaching a predetermined depth, reaching a predetermined elapsed time from deployment, and/or descending into contact with a seabed. See specific steps illustrated in FIG. 6 using conventional flowchart symbols for steps, decisions, and branches.

The apparatus includes at least one controller 50 coupled to a plurality of marine parameter value sensors 31 for sensing and recording in the data memory 33 a plurality of said marine parameter values. The sensors advantageously include a sensor for ambient water pressure, a timer, and a detector from at least one of the group consisting of fluorescence, turbidity, salinity, pH, concentration of biological tissue, concentration of petroleum products, concentration of petroleum dispersant. In the embodiment shown in FIG. 5, a CT and a fluorometer are coupled in data communication with the processor unit, which according to a stored program collects and processes the data, storing the data in the MicroSD storage module (i.e., data memory). Other data including motion and location data from the IMU module and the GPS module and time and depth readings associated with stored data values, are also processed and stored. The data values are managed to facilitate association of the data points (e.g., location and parameter values as a function of depth) for later analysis together with data collected by other autonomous units and data from other sources, such as prevailing currents.

The controller is responsive to at least one of the marine parameter value sensors and the timer, for triggering at least one parameter value measurement as a function of at least one of elapsed time from deployment, repetitive incremental elapsed time, measurement of a predetermined parameter value, and repetitive incremental change in a parameter value. See FIG. 6.

The controller advantageously is programmed and operative to trigger recording and storage of at least a subset of the plurality of said marine parameter values at predetermined increments of at least one of elapsed time and apparatus depth, during at least one said descending phase and at least one said ascending phase 42, 43, and preferably both phases. See FIG. 4.

The controller can be variably programmable to execute at least one of a measurement sequence and a descending/ascending phase sequence according to stored values, namely to select among two or more specific sequences of operation. FIG. 6.

The apparatus advantageously includes a communications unit 55 operable to provide at least one of a recovery beacon signal, a downloaded location code and a data upload signal. FIG. 4.

The communications unit 55 is coupled to the data memory (33 via 50 in FIG. 5) and the apparatus is configured to upload contents from the data memory 33 to a remote transponder when reaching the marine surface following at least one said ascending phase 43. See FIGS. 4 and 6.

In one embodiment, the variable buoyancy device 35 comprises a ballast weight mechanism 35 with a weight 47 releasable by operation of an electromagnetic device 48, operative in the descending phase 42 to produce the negative buoyancy and jettisoned when switching to the positive buoyancy for the ascending phase 43. In this arrangement jettisoning the weight precludes a subsequent descending phase 43. In alternative embodiments buoyancy can be adjusted using pressurized gas for displacing water from a ballast tank to achieve positive buoyancy, and being adapted for plural sequences of descent and ascent. FIG. 5 illustrates the use of a mechanical connection to a drop weight through a linear actuator, for example using a magnet but optionally operating a releasable mechanical clasp. Alternatively, linear actuators can be provided to operate one or more valves on a pressurized gas ballast unit (not shown).

The invention likewise encompasses a method for modeling ambient conditions in a body of water (FIGS. 1, 3, 4), including providing at least one and preferably a plurality of autonomous marine data collection apparatus 22 as described, each said autonomous apparatus including a data collection unit 25 configured for subsurface deployment, with an on-board power supply 27, a marine parameter value sensor 31, a data memory 33 and a variable buoyancy device 35. Each said apparatus is configured to maintain a negative buoyancy condition during at least one descending phase 42 of the subsurface deployment of the data collection apparatus, in which the data collection apparatus 22 descends autonomously through a marine water column, and to switch into a positive buoyancy condition during at least one ascending phase 43 of the subsurface deployment, in which the data collection apparatus ascends autonomously to a marine surface 45, wherein the parameter value sensor of each said apparatus is configured to measure at least one marine parameter value encountered during at least one of the descending and ascending phases and to record said marine parameter value in the data memory (FIG. 6).

Preferably, a plurality of said autonomous marine data collection apparatus are deployed at spaced locations over a marine surface area (FIG. 1, FIG. 4) such that each said autonomous marine data collection apparatus records and stores in the data memory 33 thereof subsurface parameter values in a water column associated with position at which said apparatus is deployed, then descended while taking measurements and ascended to report. Data is then collected from the data memories 33 of said plurality of autonomous data collection apparatus after at least one ascent to the marine surface. The data and/or an analysis thereof, characterizes a volume of water under the spaced locations, being useful in an exemplary scenario to assess oil spill conditions and the effects of amelioration efforts such as subsea dispersant injection.

The autonomous data collection apparatus can be programmable according to requirements, especially to autonomously sample plural said marine parameter values at one of spaced times and spaced depths during at least one of the descending and ascending phases 42, 43 (FIGS. 1, 3, 4). Although an embodiment wherein the data is obtained by retrieving the apparatus is disclosed, the collecting data step preferably includes electronically uploading contents of the data memories 33 of the plurality of autonomous data collection apparatus, for example over a satellite network (FIG. 4). In the embodiment shown in FIG. 5, one or more power and/or signal connectors allows the option of direct hardwired connection to the device for programming, battery charging, data retrieval, and a WiFi module provides for local wireless data connectivity to supplement the Iridium/GPS antenna and communication arrangements for remote connectivity. Although data pathways are thus provided, especially for programming and data reporting, it is an aspect of the device that data collection excursions are conducted autonomously.

In these exemplary embodiments, the data collection apparatus are arranged to obtain their location from a GPS system or the like immediately after deployment into the descending phase and again after the ascending phase upon return to the surface. However, the data collection apparatus are substantially or totally autonomous, namely operable independently of signaling from a remote device and independently of physical attachment to the remote device, during the descending and ascending phases.

Switching from the negative buoyancy condition to the positive buoyancy condition can involve at least one of releasing a ballast weight and altering buoyancy by adding or displacing sea water from a ballast tank, the latter example permitting successive descents and ascents.

The invention has been described with reference to a number of alternative embodiments and scenarios for deployment, which are exemplary. The invention is not limited to the exemplary alternatives and is capable of other embodiments within the scope of the appended claims.

What is claimed is:

1. An autonomous marine data collection apparatus, comprising:
   a data collection unit configured for subsurface deployment, with an on-board power supply, a marine parameter value sensor, a timer, a data memory, a variable buoyancy device, and a controller;
   wherein the variable buoyancy device is configured to maintain a negative buoyancy condition for the data collection apparatus during at least one descending phase of the subsurface deployment of the data collection apparatus, in which the data collection apparatus descends autonomously through a marine water column, and to switch into a positive buoyancy condition during at least one ascending phase of the subsurface deployment, in which the data collection apparatus ascends autonomously to a marine surface;
   wherein the marine parameter value sensor is configured to measure at least one marine parameter value encountered during at least one of the descending and ascending phases and to record said marine parameter value in the data memory;
   wherein the controller is coupled to the marine parameter value sensor for sensing and recording in the data memory said marine parameter value;
   wherein the controller is responsive to the marine parameter value sensor and the timer, for triggering at least one parameter value measurement as a function of at least one of elapsed time from deployment, repetitive incremental elapsed time, measurement of a predetermined parameter value and repetitive incremental change in a parameter value; and
   wherein the data memory is configured for extraction of data in the data memory following the subsurface deployment.

2. The apparatus of claim 1, wherein the apparatus is contained in a housing affixed to the variable buoyancy device and the variable buoyancy device is configured for one of releasing a ballast weight and inflating a ballast plenum, when switching into the positive buoyancy condition.

3. The apparatus of claim 2, wherein the variable buoyancy device apparatus is triggered by at least one of reaching a predetermined depth, reaching a predetermined elapsed time from deployment and descending into contact with a seabed.

4. The apparatus of claim 3, wherein the variable buoyancy device comprises a ballast weight mechanism releasable by operation of an electromagnetic device, operative in the descending phase to produce the negative buoyancy and jettisoned when switching to the positive buoyancy.

5. The apparatus of claim 1, wherein the controller is coupled to a plurality of marine parameter value sensors for sensing and recording in the data memory a plurality of marine parameter values, the plurality of marine parameter value sensors including a sensor for ambient water pressure and a detector from at least one of the group consisting of fluorescence, turbidity, salinity, pH, concentration of biological tissue, concentration of petroleum products, and concentration of petroleum dispersant.

6. The apparatus of claim 5, wherein the controller is operative to record at least a subset of the plurality of said marine parameter values at predetermined increments of at least one of elapsed time and apparatus depth, during at least one said descending phase and at least one said ascending phase.

7. The apparatus of claim 6, wherein the controller is variably programmable to execute at least one of a measurement sequence and a descending/ascending phase sequence according to stored values.

8. The apparatus of claim 1, further comprising a communications unit operable to provide at least one of a recovery beacon signal and a data upload signal.

9. The apparatus of claim 8, wherein the communications unit is coupled to the data memory and configured to upload contents from the data memory to a remote transponder when reaching the marine surface following at least one said ascending phase.

10. A method for modelling ambient conditions in a body of water, comprising:

provide a plurality of autonomous marine data collection apparatuses, each including a data collection unit configured for subsurface deployment, with an on-board power supply, a marine parameter value sensor, a data memory and a variable buoyancy device, each said apparatus being configured to maintain a negative buoyancy condition during at least one descending phase of the subsurface deployment of the data collection apparatus, in which the data collection apparatus descends autonomously through a marine water column, and to switch into a positive buoyancy condition during at least one ascending phase of the subsurface deployment, in which the data collection apparatus ascends autonomously to a marine surface, wherein the parameter value sensor of each said apparatus is configured to measure at least one marine parameter value encountered during at least one of the descending and ascending phases and to record said marine parameter value in the data memory;

deploying a plurality of said autonomous marine data collection apparatuses at spaced locations over a marine surface area such that each said autonomous marine data collection apparatus records and stores in the data memory thereof subsurface parameter values in a water column associated with the location at which said apparatus is deployed; and, collecting data from the data memories of said plurality of autonomous data collection apparatuses after at least one ascent to the marine surface, and characterizing a volume of water under the spaced locations.

11. The method of claim 10, further comprising programming the autonomous data collection apparatus to sample plural said marine parameter values at one of spaced times and spaced depths during at least one of the descending and ascending phases.

12. The method of claim 10, wherein said collecting data step comprises electronically uploading contents of the data memories of the plurality of autonomous data collection apparatus.

13. The method of claim 10, wherein the autonomous data collection apparatus are operable independently of signaling from a remote device and independently of physical attachment to the remote device during the descending and ascending phases.

14. The method of claim 10, wherein switching from the negative buoyancy condition to the positive buoyancy condition comprises releasing a ballast weight.

15. An autonomous marine data collection apparatus, comprising:

a data collection unit configured for subsurface deployment, with an on-board power supply, a marine parameter value sensor, a data memory and a variable buoyancy device;

wherein the variable buoyancy device is configured to maintain a negative buoyancy condition for the data collection apparatus during at least one descending phase of the subsurface deployment of the data collection apparatus, in which the data collection apparatus descends autonomously through a marine water column, and to switch into a positive buoyancy condition during at least one ascending phase of the subsurface deployment, in which the data collection apparatus ascends autonomously to a marine surface;

wherein the apparatus is contained in a housing affixed to the variable buoyancy device and the variable buoyancy device is configured for one of releasing a ballast weight and inflating a ballast plenum, when switching into the positive buoyancy condition;

wherein the variable buoyancy device apparatus is triggered by at least one of reaching a predetermined depth, reaching a predetermined elapsed time from deployment and descending into contact with a seabed;

wherein the variable buoyancy device comprises a ballast weight mechanism releasable by operation of an electromagnetic device, operative in the descending phase to produce the negative buoyancy and jettisoned when switching to the positive buoyancy;

wherein the marine parameter value sensor is configured to measure at least one marine parameter value encountered during at least one of the descending and ascending phases and to record said marine parameter value in the data memory; and wherein the data memory is configured for extraction of data in the data memory following the subsurface deployment.

16. The apparatus of claim 15, further comprising a communications unit operable to provide at least one of a recovery beacon signal and a data upload signal.

17. The apparatus of claim 16, wherein the communications unit is coupled to the data memory and configured to upload contents from the data memory to a remote transponder when reaching the marine surface following at least one said ascending phase.

18. The apparatus of claim 15, comprising a controller coupled to a plurality of marine parameter value sensors for sensing and recording in the data memory a plurality of marine parameter values and to a timer, the plurality of marine parameter value sensors including a sensor for ambient pressure and a detector from at least one of the group consisting of fluorescence, turbidity, salinity, pH, concentration of biological tissue, concentration of petroleum products, and concentration of petroleum dispersant.

19. The apparatus of claim 18, wherein the controller is responsive to at least one of the marine parameter value sensors and the timer, for triggering at least one parameter value measurement as a function of at least one of elapsed time from deployment, repetitive incremental elapsed time, measurement of a predetermined parameter value and repetitive incremental change in a parameter value.

20. The apparatus of claim 19, wherein the controller is operative to record at least a subset of the plurality of said marine parameter values at predetermined increments of at least one of elapsed time and apparatus depth, during at least one said descending phase and at least one said ascending phase.

* * * * *